United States Patent

Ueberle

[11] Patent Number: 5,810,748
[45] Date of Patent: Sep. 22, 1998

[54] DEVICE FOR LOCATING AND CRUSHING CONCREMENTS

[75] Inventor: Friedrich Ueberle, Gilching, Germany

[73] Assignee: Dornier Medizintechnik GmbH, Germany

[21] Appl. No.: 871,682

[22] Filed: Jun. 9, 1997

[30] Foreign Application Priority Data

Jun. 7, 1996 [DE] Germany .................. 196 22 919.7

[51] Int. Cl.⁶ .................................................. A61B 17/22
[52] U.S. Cl. .................................................. 601/4; 600/439
[58] Field of Search ............................ 601/3, 4; 600/439

[56] References Cited

U.S. PATENT DOCUMENTS

| Re. 34,964 | 6/1995 | Okazaki | 600/439 |
| 5,048,527 | 9/1991 | Okazaki | 600/439 |
| 5,065,762 | 11/1991 | Ifflaender et al. | 600/439 |
| 5,165,412 | 11/1992 | Okazaki | 600/439 |
| 5,305,731 | 4/1994 | Buchholtz | 600/439 |
| 5,419,335 | 5/1995 | Hartmann et al. | 600/439 |
| 5,699,804 | 12/1997 | Rattner | 601/4 |

*Primary Examiner*—Brian Casler
*Attorney, Agent, or Firm*—Evenson, McKeown, Edwards & Lenahan, P.L.L.C.

[57] ABSTRACT

The device for locating and crushing concrements has a shock wave generator, a coupling arrangement and a locating arrangement. The coupling arrangement consists of a ring-shaped coupling cushion which has a central passage and essentially symmetrically surrounds the locating arrangement.

16 Claims, 2 Drawing Sheets

DEVICE FOR LOCATING AND CRUSHING CONCREMENTS

This application claims the priority of German patent application 196 22 919.7, the disclosure of which is expressly incorporated by reference herein.

BACKGROUND AND SUMMARY OF THE INVENTION

The present invention relates to a device for locating and crushing concrements in a patient's body by means of a shock wave generator, with a coupling arrangement for transmitting the shock waves into the patient's body and a locating arrangement for precisely determining the position of the concrement.

Such devices, which are also called lithotriptors, are known in many forms. Thus, German Patent Document DE-OS 3532678 describes such a lithotriptor whose shock waves are transmitted by way of a liquid in a flexible liquid flow path which comes into direct or indirect contact with the patient's body, so that such shock waves are focussed on the located stone. The patient lies on a surface which is provided with a window, below which the shockwave generator with the flexible liquid flow path is arranged. The liquid, which is sealed off to the outside, through the window, comes in direct contact with the patient's body surface which is to be treated ultrasonically and dips into the window Alternatively, it comes in contact with the patient's body surface by way of a membrane sealing off the flow path.

German Patent Document DE-OS 4124259 relates to a lithotriptor having a sound wave generator and a flow path which is filled with a coupling liquid. A membrane is arranged between the sound generator and the patient's body. The flow path has a first space, closed off toward the outside, between the sound wave generator and the membrane as well as a second open space between the membrane and the patient's body, which can be closed off by the patient's body.

In these known lithotriptors, it is a disadvantage that the sound waves emitted by the locating device to determine the exact position of the concrement situated in the patient's body, which are normally aimed at the patient's body coaxially to the axis of the shock waves radiated later, must penetrate the membrane between the coupling arrangement and the patient (holding back the coupling liquid), when entering the body as well as after reflection by the concrement. Thus, the image quality of the locating arrangement is impaired.

European Patent Document EP A 441 997 discloses a shock wave generator for generating shock waves in an acoustic expansion medium. For locating purposes, an ultrasound applicator, which has at least one ultrasound transducer, introduces ultrasonic waves into the acoustic propagation medium. A substance disposed in front of at least one portion of the area of the ultrasound applicator in the propagation path of the shock waves, has an acoustic impedance which differs considerably from that of the acoustic propagation medium. The ultrasound applicator consists of a hollow-cylindrical tube-shaped housing which accommodates the ultrasound transducer. On its end facing the patient, it has a dome-shaped closing part in which the sound emission window for locating is provided. The applicator projects into the coupling cushion but, in the process, is also surrounded on all sides in the membrane facing the patient's body (and enclosing the coupling liquid), so that the locating waves emitted by the applicator must also pass twice through this membrane in the direction of the concrement.

It is an object of present invention to provide an improved image quality of the locating arrangement, for the precise determination of the position of the concrement by means of a simple construction.

This object is achieved by means of the coupling arrangement according to the invention in the form of a ring-shaped coupling cushion with a central passage which surrounds the locating arrangement essentially asymmetrically. The locating arrangement is inserted into the passage in the coupling cushion displaceably in the axial direction, as well as rotatably about the longitudinal axis. Because of the liquid inlet and outlet connected with the locating arrangement and leading into the passage, the sound waves emitted by the locating arrangement can enter the body through the membrane in an undisturbed and unhindered manner, and can be reflected by the concrement so that a clearer and more exact image of the position of the concrement is obtained. Through the liquid inlet and outlet, the space between the surface of the locating arrangement facing the patient and the patient's body surface is filled with a suitable coupling liquid which is not connected with the coupling liquid in the coupling cushion. This has the advantage that only the small amount of coupling liquid situated between the patient's body surface and the locating arrangement has to be exchanged during each change of patient.

Other objects, advantages and novel features of the present invention will become apparent from the following detailed description of the invention when considered in conjunction with the accompanying drawings.

DETAILED DESCRIPTION OF THE DRAWINGS

Figure 1:
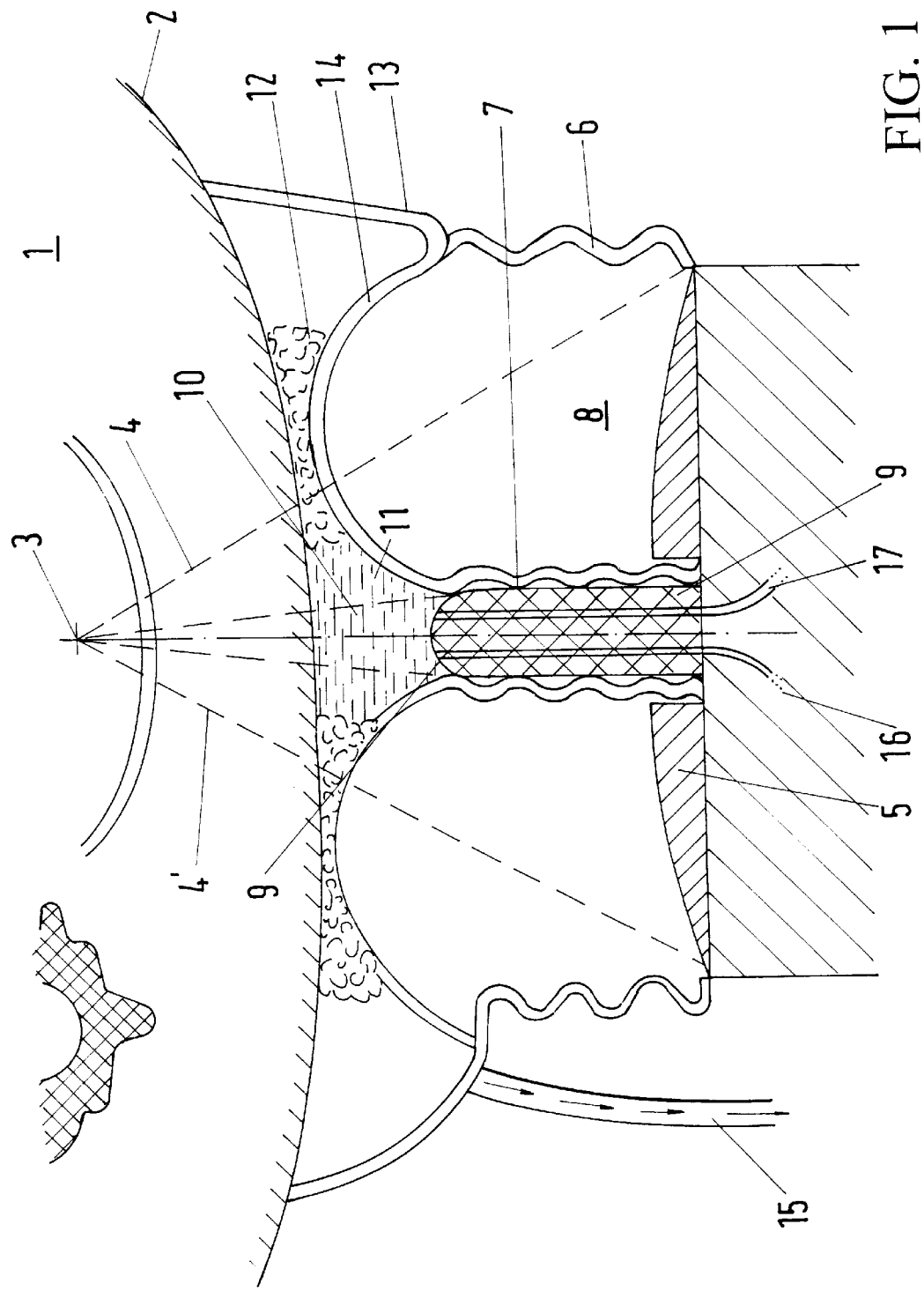
FIG. 1 is a sectional view of the important parts of a device according to the invention for locating and crushing concrements in a patient's body.
Figure 2:
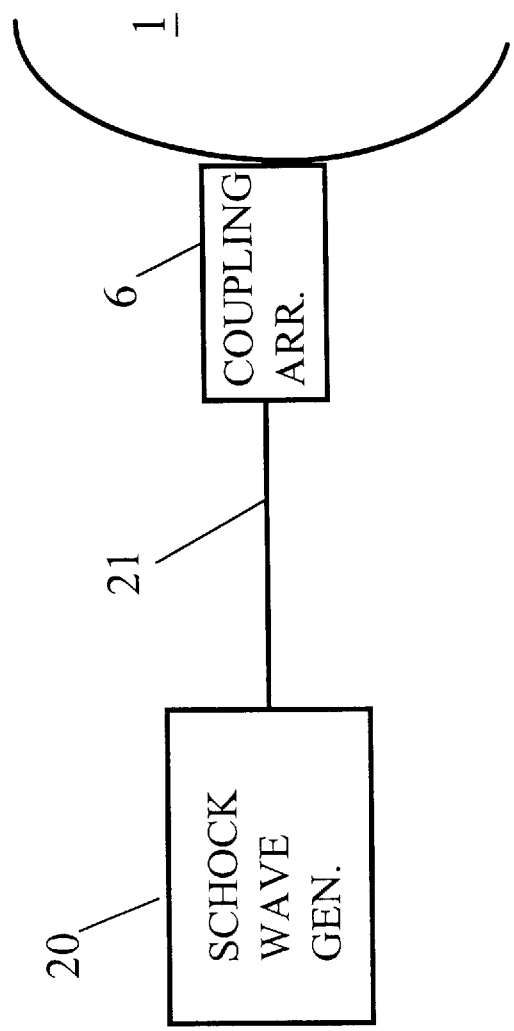
FIG. 2 is a schematic depiction of the device according to the invention.

In FIG. 1, reference number 1 indicates a part of the patient's body and reference number 2 indicates its surface (that is, the skin). A concrement 3 to be crushed, such as a kidney stone, is situated in the patient's body 1. The lithotriptor, which is shown only partially in FIG. 1, includes a shock wave generator 20, a pressure line 21 (FIG. 2) and a coupling arrangement 6 for transmitting the shock waves, whose edge rays or envelope are indicated by broken lines and have the reference number 4 and 4'. A locating arrangement 9 is provided for precisely determining the position of the concrement 3 in the patient's body 1. The shock waves generated by the shock wave generator 20 and emitted in parallel are bundled in the direction of the concrement 3 by means of a focussing arrangement 5 which is known per se.

The schematically indicated locating arrangement 9 permits precise determination of the position of the concrement 3, and thus exact focussing of the shock waves. In order that the ultrasonic waves may be radiated into the patient's body as undisturbed as possible, in the present invention, the coupling arrangement is constructed in the form of a ring-shaped elastically deformable coupling cushion 6 with a central passage 7. The coupling cushion 6 consists of flexible ring-shaped bellows 6A and an elastically deformable ring-shaped membrane 14 which closes this annulus off in the direction of the patient 1. It is filled with a suitable coupling liquid 8 for introducing the shock waves 8, and is connected in a liquid-tight manner with the focussing arrangement 5 of the shock wave generator.

Advantageously, an elastic surrounding collecting trough 13 is provided on the exterior of the ring-shaped coupling cushion 6. This collecting trough is designed such that, when the coupling cushion 6 rests against the patient's body 1, its free edge also rests against the body so that an annulus formed by the membrane 14 of the coupling cushion and the collecting trough 13 can also be filled with a coupling liquid. The collecting trough 13 is optionally provided with an inlet and/or outlet 15.

A circular gel disk 12 may be provided between the elastic membrane 14 of the coupling cushion and the patient's skin 2, for improving the transmission of the shock waves and for sealing off the space 10 between the locating arrangement 9 and the body surface 2, extending the passage 7. The space 10 may be filled with a suitable liquid 11 used for the introduction of the shock waves generated by the locating arrangement 9, into the patient's body. For this purpose, the locating arrangement 9 is advantageously provided with an inlet 16 and an outlet 17, for filling the coupling liquid 11 into the space 10.

It is apparent that the coupling liquid 8 in the coupling cushion 6, for the introduction of the shock waves from the shock wave generator, need not be exchanged when the patient changes, because this liquid is not in contact with the patient himself; rather, it is separated from him by the membrane 14 and optionally by the gel disk 12. Only the small amount of liquid 11 present in space 10 is removed for each change of patient or after the conclusion of the treatment.

Preferably, the inlet and the outlet for the space 10 are provided with a liquid pump. The inlet and outlet for the collecting trough 13 may also be provided with a suitable pump. It is particularly advantageous for the locating arrangement 9, arranged in the recess 7 in the ring-shaped coupling cushion 6, to be displaceable in the axial direction and rotatable about its longitudinal axis by means of an operating device (not shown). A suitable operating device for the axial displacement of the locating arrangement 9 may be provided simply and at minimal cost, by designing the exterior wall of the part of the locating arrangement 9 that penetrates the recess 7 so that, when pressure acts upon the coupling cushion 6, the wall of the coupling cushion 6 surrounding the recess 7 moves the locating arrangement 9 in the direction of the patient 1.

Advantageously, the locating arrangement 9 is provided with a sensor 18 which determines its position relative to the coupling cushion, and therefore to the patient 1, and reports it to a monitoring device of the lithotriptor.

An arrangement of the locating direction which is diagonal with respect to the shock wave axis is also possible. In this case, the central part of the shock wave source is switched off less intensely by the locating direction. The coupling cushion may also be filled with a gel and closed by means of a gel plug, so that the inlet and the outlet are eliminated.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. A device for locating and crushing concrements in a patient's body, comprising:
    a shock wave generator for generating shock waves to be transmitted into a patient's body;
    a locating arrangement for precisely determining the position of the concrement; and
    a shock wave coupling arrangement for coupling said shock waves into the patient's body, wherein
    the shock wave coupling arrangement has a ring-shaped coupling cushion which is provided with a central passage having an opening that surrounds the locating arrangement;
    the ring shaped cushion is connected in a liquid tight manner with the shock wave generator and has a liquid inlet and outlet; and
    the locating arrangement has a liquid inlet and a liquid outlet, both of which lead into the coupling cushion in proximity to an end of the locating arrangement facing the patient, in a space between the patient and a recess in the coupling cushion.

2. Device according to claim 1 wherein the coupling cushion rests against a gel ring surrounding the central passage.

3. Device according to claim 1 wherein an exterior of the coupling cushion is provided with an elastic surrounding collecting trough having a free edge which is adapted to rest against the patient's body.

4. Device according to claim 3 wherein the collecting trough has a liquid inlet and a liquid outlet connected to a pump.

5. Device according to claim 1 wherein the locating arrangement arranged in the recess is displaceable in an axial direction and rotatable about a longitudinal axis.

6. Device according to claim 1 wherein an exterior wall of the locating arrangement, which contacts an interior wall of the coupling cushion, is shaped such that, when the coupling cushion is acted upon by pressure, the locating arrangement is moved in the direction of the patient.

7. Device according to claim 1 wherein the locating arrangement has a location sensor.

8. Device according to claim 1 wherein the locating arrangement is adapted to be coupled to the patient by way of a gel plug which extends approximately to an edge of the coupling cushion.

9. Device according to claim 1 wherein the locating arrangement is arranged at an angle with respect to the shock source.

10. Device according to claim 1 wherein the locating arrangement arranged in the recess is rotatable about a longitudinal axis.

11. For use with a device for locating and crushing concrements in a patient's body, having a shock wave generator for generating shock waves to be transmitted into the patient's body and a locating arrangement for precisely determining a position of the concrement, a shock wave coupling arrangement for coupling said shock waves into the patient's body, said shock wave coupling arrangement comprising:
    a ring-shaped coupling cushion which is provided with a central passage, for surrounding the locating arrangement; wherein the ring shaped coupling cushion is adapted to be connected in a liquid tight manner with the shock wave generator ; and the coupling cushion has a liquid inlet and a liquid outlet, both of which lead into a space between the patient and a recess in the coupling cushion.

12. Device according to claim 11 wherein the coupling cushion rests against a gel ring surrounding the central passage.

13. Device according to claim 10 wherein an exterior of the coupling cushion is provided with an elastic surrounding collecting trough having a free edge which is adapted to rest against the patient's body.

14. Device according to claim 13 wherein the collecting trough has a liquid inlet and a liquid outlet connected to a pump.

15. Device according to claim 11 wherein an interior wall of the coupling cushion is adapted to contact an exterior wall of the locating arrangement for moving the locating arrangement in a direction of the patient, when the coupling cushion is acted upon by pressure.

16. Device according to claim 11 wherein the coupling cushion is adapted to be coupled to the patient by way of a gel plug which extends approximately to an edge of the coupling cushion.

* * * * *